United States Patent [19]

Konicek

[11] Patent Number: 4,615,486

[45] Date of Patent: Oct. 7, 1986

[54] AUTOMATIC DOOR-ACTIVATED AIR FRESHENER

[75] Inventor: Tim R. Konicek, Racine County, Wis.

[73] Assignee: S. C. Johnson & Son, Inc., Racine, Wis.

[21] Appl. No.: 795,153

[22] Filed: Nov. 5, 1985

Related U.S. Application Data

[62] Division of Ser. No. 655,173, Sep. 27, 1984.

[51] Int. Cl.$^4$ ............................................. A61L 9/04
[52] U.S. Cl. ...................................... 239/274; 239/43; 222/162
[58] Field of Search ..................... 239/34, 35, 37–43, 239/274, 289; 222/162; 137/38

[56] References Cited

U.S. PATENT DOCUMENTS

| | | | |
|---|---|---|---|
| 1,104,972 | 7/1914 | Dover | 137/38 |
| 2,728,608 | 12/1955 | Marini | 222/162 |
| 2,991,517 | 7/1961 | Bundy | 239/43 |
| 3,737,104 | 6/1973 | Schneider | 239/274 |

Primary Examiner—Joseph F. Peters, Jr.
Assistant Examiner—Michael J. Forman

[57] ABSTRACT

This relates to an air freshener which is intended to be mounted on a swinging member, such as a door. The air freshener includes an upper reservoir and a lower liquid perfume distributor or generator pad. The reservoir will carry a dispensing valve, preferably in the bottom wall thereof. The dispensing valve includes an over center valve member which will tilt from one position to another when the air freshener is moved. When actuated, the valve member will swing from one tilted orifice closing position to a momentary on center dispensing position and then to its other off-center tilted position closing the valve orifice.

3 Claims, 8 Drawing Figures

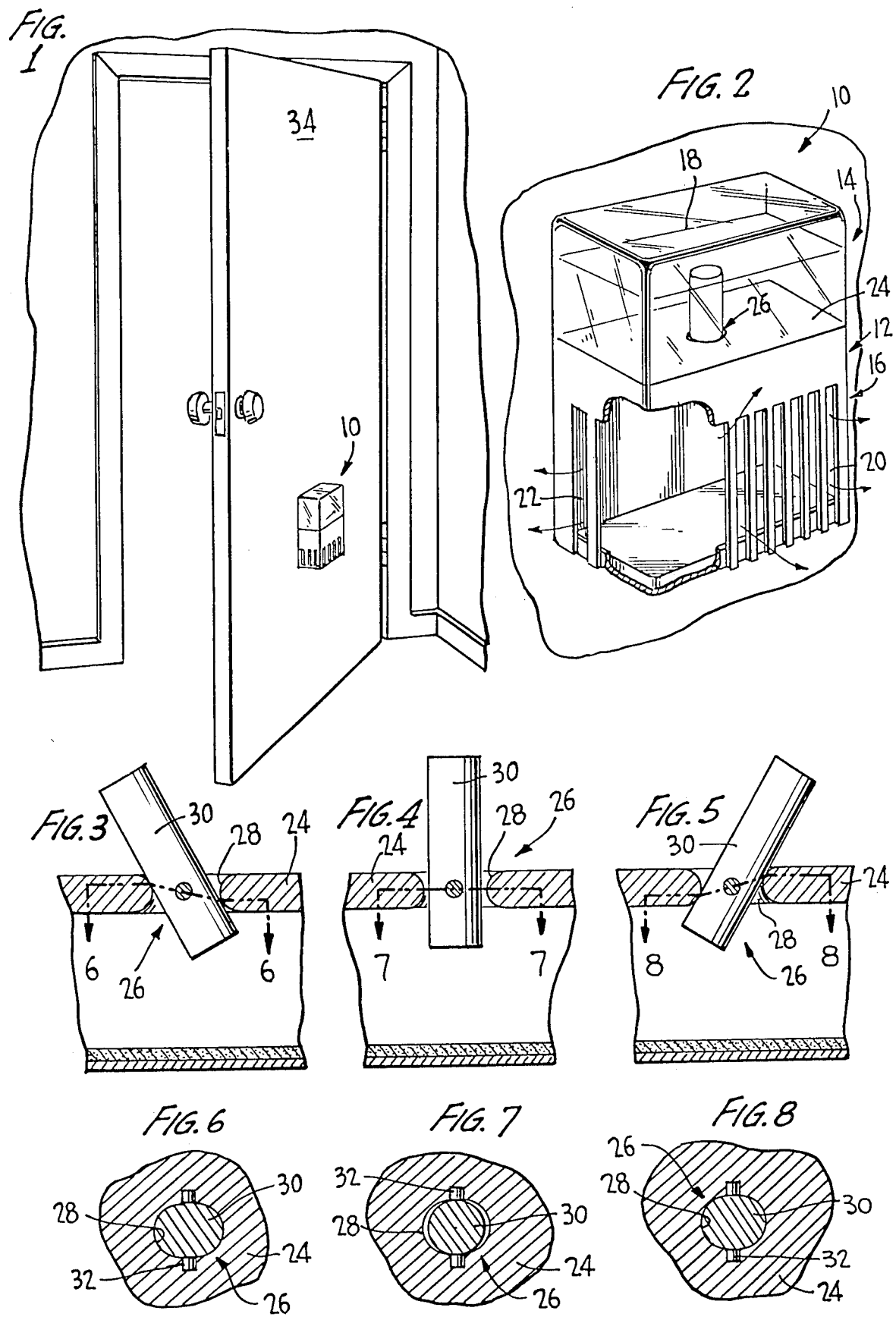

AUTOMATIC DOOR-ACTIVATED AIR FRESHENER

This is a divisional of co-pending application Ser. No. 655,173 filed on 9/27/84.

This invention relates in general to new and useful improvements in air fresheners, and more particularly to an air freshener which may be mounted on a door for swinging therewith and which is automatically actuated to dispense liquid perfume upon each actuation of the door.

This invention in particular relates to an air freshener having a motion-driven valve that, when actuated, will release a controled amount of liquid perfume. The liquid perfume will be dispensed onto a distributor which may be in the form of a paper or like pad.

In accordance with the invention there is provided a normally closed valve which, when subjected to motion, swings to an on-center position wherein it is opened and then swings beyond that on-center position to a second closed position and, while at that on-center position, dispenses a prescribed amount of liquid from an adjacent reservoir. Most particularly it is preferred to incorporate the valve in the bottom wall of a liquid reservoir.

The valve per se includes a liquid passage or orifice and a valve member which is pivoted below its center of gravity so that the valve member always tends to assume a tilted position wherein it fully closes the orifice. When the valve member is subject to motion which will effect rocking thereof, it will move from a first tilted position to an on-center position where it does not fill and close the orifice and then to a second tilted position where once again it fills and closes the orifice. When in the on-center position, liquid will be dispensed.

Accordingly, the primary objects of the invention are to provide an air freshener which is activated by motion utilizing the aforesaid motion-actuated valve and to the valve per se. Other objects and advantages reside in the details of construction and operation as will be more fully described and claimed hereinafter, reference being made to the accompanying drawing forming a part hereof, wherein like numerals refer to like parts throughout, and in which FIG. 1 is a perspective view showing a conventional door having mounted thereon an air freshener formed in accordance with this invention.

FIG. 2 is an enlarged perspective view showing specifically the overall details of the air freshener with parts broken away and shown in section.

FIG. 3 is a vertical sectional view taken through a wall of the air freshener of FIG. 2, and shows the details of the valve formed in that wall.

FIG. 4 is a sectional view similar to FIG. 3 and shows the valve in a dispensing position.

FIG. 5 is a sectional view similar to FIG. 3 but shows the valve in a second closed position.

FIG. 6 is a horizontal sectional view taken generally along the line 6—6 of FIG. 3 and shows the relationship of a valve member with respect to the valve passage or orifice in the closed position of FIG. 3.

FIG. 7 is a horizontal sectional view similar to FIG. 6 but taken along the line 7—7 of FIG. 4 and shows the relationship of the valve and the orifice in open position of the valve.

FIG. 8 is another horizontal sectional view similar to FIG. 6 but taken along the line 8—8 of FIG. 5 and shows the valve in its other closed position.

Referring now to the drawings in detail, reference is made to FIG. 2 wherein there is illustrated the air freshener which is the subject of this invention, the air freshener being generally identified by the numeral 10. The air freshener 10 includes a housing 12 which may be formed from a suitable plastic material using any suitable molding method such as injection molding or thermoforming, and preferably includes an upper part 14 and a lower part 16. The upper part 14 is preferably formed of a transparent material and defines a reservoir. The reservoir will normally contain a supply of liquid perfume 18 and when the upper portion 14 which forms the reservoir is formed of a transparent material, one can visually determine when the supply of liquid perfume has been exhausted.

The lower housing portion 16 may be of any design but is provided with walls of an open work so as to define a plurality of openings 20 through which air may be circulated. A distributor 22 is mounted within the lower housing portion 16 for receiving liquid perfume from the reservoir. The distributor is in the form of a generator pad which may be formed of paper or like material. The generator pad or distributor 22 delivers perfume over a period of time and with a burst each time a new quantity of the liquid perfume 18 is delivered thereto.

In order that the liquid perfume 18 may be periodically dispensed to the distributor 22, there is mounted in a bottom wall 24 of the upper housing portion 14 a valve which is generally identified by the numeral 26 and which is best illustrated in FIGS. 3 through 8.

Referring now to FIGS. 4 and 7, it will be seen that the wall 24 has formed therethrough a valve passage or orifice 28 which is generally elliptical in outline. The orifice 28 will also have a rounded wall as is best shown in FIG. 4.

The valve 26, of which the orifice 28 is a part, also includes a valve member 30. The valve member 30 is of a circular cross-section and is in the form of an elongated rod which may have a suitable weight (not shown) in its upper end. The valve member 30 is carried by a pivot pin or like pivot element 32 which extends across the short dimension or width of the orifice 28 as is shown in FIG. 7. It is to be noted that the pivot pin 32 is disposed below the center of gravity of the valve member 30 so that the valve member 30 will normally not assume an upstanding position as is shown in FIGS. 4 and 7.

When the valve member 30 is in its upstanding position, there will be a clearance between the valve member 30 and the wall of the orifice 28. This clearance has been exaggerated in the drawings, and will be such that when the valve member 30 is in the upstanding liquid-dispensing position only drops will pass on opposite sides of the valve member as is shown in FIG. 4. The drops of liquid perfume 18 which are dispensed when the valve member 30 is in its upstanding position will fall on the generator pad 22.

Referring now to FIGS. 3 and 6, it will be seen that the valve member 30 is illustrated in one of its "at-rest" positions. The valve member 30 is tilted to the left and in its tilted position will have an elliptical cross-section in the general plane of the wall 24 which corresponds to the cross section of the orifice 28 so as to completely close the orifice and prevent dispensing of the liquid perfume 18.

When there is motion of the valve 26 to the left as viewed in FIG. 3, the valve member 30 will swing to the right to its upstanding position of FIG. 4 and while in that position will momentarily dispense drops of the liquid perfume 18. The valve member 30 will then move to an "over center" position and due to the pivotal mounting thereof below its center of gravity will continue to the right to the position shown in FIG. 5, at which time it will again completely clsoe the orifice 28. When the valve 26 is moved to the right, the opposite of this motion will be repeated.

Although the orifice 28 has been illustrated as being elliptical in outline and the valve member 30 circular in cross-section, it is to be understood that other accommodations or cross-sections are feasible. Also, it is possible that a continuous slow delivery of fluid may be desired with a burst when the unit is activated. In this instance, the fit between valve member 30 and orifice 28 can be such as to allow for some small dispensing of fluid in the closed position.

It is also pointed out that while the valve 26 has particular usage in conjunction with an air freshener, it is to be understood that the valve 26 could be utilized in other environments.

Returning now to FIG. 1, it will be seen that the air freshener 10 is conveniently mounted on a door 34 which controls access into a room. When the room is not being used, the door 34 will not be opened and closed and the air freshener 10 for all practical purposes will remain dormant. However, by positioning the axis of the pivot 32 parallel to the plane of the door 34, upon each movement of the door 34, either towards open position or towards a closed position, the valve member 30 will be actuated so as to dispense the liquid perfume 18 onto the generator pad 22.

At this time it is pointed out that the release rate for the liquid perfume 18 can be controlled in a number of manners including liquid viscosity control, liquid rheology control, orifice size, valve lag time, and distance of valve travel.

Although only a preferred embodiment of the air freshener has been specifically illustrated and described herein, it is to be understood that minor variations may be made in the construction of both the air freshener per se and the valve without departing from the spirit and scope of the invention as defined by the appended claims.

It is claimed:

1. A door-actuated efficacious vapor system comprising a door mounted for swinging movement, a motion actuated air freshener mounted on said door for swinging movement with said door, said air freshener including an upper liquid reservoir and a lower distributor, a liquid passage between said reservoir and said distributor for gravity supplying liquid from said reservoir to said distributor, and a motion-actuated, normally closed valve in said liquid passage for permitting momentary liquid flow from said reservoir through said liquid passage in response to movement of said air freshener, said door forming means for both actuating said valve and causing air currents flowing across said distributor, wherein said valve includes said liquid passage defining a valve passage of greater length than width, a valve member positioned in said valve passage and pivotally mounted on a pivot having an axis in the direction of said width, said valve member having a major portion of the weight thereof positioned above said pivot whereby said valve member normally assumes a tilted position, said valve member and said valve passages being of related cross-sections such that when said valve member is in a tilted position said valve member fills and closes said valve passage and when said valve member is upright there is clearance in said valve passage around said valve member for limitd liquid flow through said valve passage.

2. A system according to claim 1 wherein said valve member is circular in cross-section and said valve passage is generally elliptical in cross-section.

3. A system according to claim 1 wherein said reservoir has a bottom wall, and said valve passage is formed in said bottom wall.

* * * * *